United States Patent [19]

Mayhew et al.

[11] Patent Number: 4,503,002

[45] Date of Patent: Mar. 5, 1985

[54] PHOSPHATE QUATERNARY COMPOUNDS

[75] Inventors: Raymond L. Mayhew, Summit; Anthony J. O'Lenick, Fairlawn, both of N.J.

[73] Assignee: Mona Industries, Inc., Paterson, N.J.

[21] Appl. No.: 492,550

[22] Filed: May 12, 1983

Related U.S. Application Data

[60] Continuation of Ser. No. 182,379, Aug. 29, 1980, abandoned, which is a division of Ser. No. 137,197, Apr. 4, 1980, Pat. No. 4,336,385, which is a continuation-in-part of Ser. No. 965,458, Nov. 30, 1978, Pat. No. 4,209,449.

[51] Int. Cl.³ ............................................. C07F 9/09
[52] U.S. Cl. .................................................... 260/945
[58] Field of Search ........................ 260/945, 670, 953

[56] References Cited

U.S. PATENT DOCUMENTS

| | | | |
|---|---|---|---|
| 3,094,549 | 6/1963 | Gurgiolo et al. | 260/953 |
| 3,205,120 | 9/1965 | Flanders | 260/953 X |
| 3,281,502 | 10/1966 | Pelletier et al. | 260/953 |
| 3,304,349 | 2/1967 | Shen | 260/920 |
| 3,324,202 | 6/1967 | Franko-Filipasic | 260/953 |

*Primary Examiner*—Anton H. Sutto
*Attorney, Agent, or Firm*—Felfe & Lynch

[57] ABSTRACT

Phosphate quaternary compounds of the formula

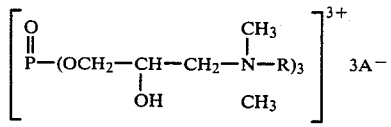

wherein R is a tertiary amine group of from 6 to 40 carbon atoms, and X is an anion.

11 Claims, No Drawings

PHOSPHATE QUATERNARY COMPOUNDS

This is a continuation of application Ser. No. 182,379, filed Aug. 29, 1980 now abandoned, which is a division of Ser. No. 137,197 filed Apr. 4, 1980, now U.S. Pat. No. 4,336,385, which is a continuation-in-part of Ser. No. 965,458, filed Nov. 30, 1978, now U.S. Pat. No. 4,209,449.

BACKGROUND OF THE INVENTION

The present invention relates to novel compositions of matter consisting of specific quaternary amine compounds linked to a fully esterified phosphate group. These phosphate quaternary amine compounds are formally cationics due to the nature of the phosphate triester.

Phosphate esters and quaternary amine compounds are known in the industry, but prior to this invention, compounds such as the phosphate quaternary amines of the invention were not suggested. These products exhibit outstanding foaming, viscosity-building, wetting, cleansing, detergency, anti-static conditioning, emulsifying and bacteriostatic properties. These highly stable compounds are well tolerated by human tissue (i.e., they exhibit exceptionally low oral toxicity and ocular irritation) hence they are eminently suited for use in cosmetic as well as industrial applications.

THE INVENTION

The novel phosphate quaternary amine compounds of this invention conform to the following general formula

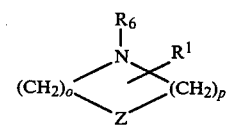

wherein R is a teriary amine radical of at least 6 carbons. This carbon atom limitation serves to include only materials of significant hydrophobic properties. The R radical can be cyclic or non-cyclic, aliphatic, aromatic or heterocyclic, X is an anion, such as halide, e.g., chloride.

In a preferred species R is an amidoamine moiety of the formula

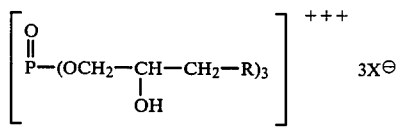

wherein
$R^1$ is alkyl, alkenyl, alkoxy, or hydroxyalkyl of from 5 to 22 carbon atoms each, or aryl or alkaryl of up to 20 carbon atoms,
$R^2$ is hydrogen or alkyl, hydroxyalkyl or alkenyl of up to 6 carbon atoms each or cycloalkyl of up to 6 carbon atoms, preferably of from 2 to 5 carbon atoms, or polyoxyalkylene of up to 10 carbon atoms,
$R^3$ and $R^4$, which may be the same or different, are selected from alkyl, hydroxyalkyl, carboxyalkyl of up to 6 carbon atoms in each alkyl moiety, and polyoxyalkylene of up to 10 carbon atoms; in addition, $R^3$ and $R^4$ taken together with the nitrogen to which they are attached, may represent an N-heterocycle, in which the Y radical is bonded to a ring atom of said N-heterocycle other than the nitrogen of the R moiety;
n is an integer from about 2 to 10.

In addition to the foregoing definitions wherein R is amidoamine, R may be an N-heterocyclic radical which may contain one additional hetero atom (e.g., oxygen or another nitrogen) and contains 5 to 6 total ring carbon atoms; optionally said heterocyclic radical may be substituted with alkyl and/or hydroxyalkyl of up to 20 carbon atoms each. Typical of such N-heterocyclic radicals are imidazolinyl, N-alkylmorpholino, alkylpyrimidino, alkyloxazolinyl, and the like. Such compounds may be represented by the formula:

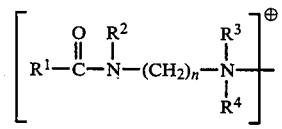

wherein
Z is N, S or O,
o is an integer from 0 to 3,
p is an integer from 1 to 3, provided that the sum of o+p is from 3 to 4;
$R^1$ is alkyl, alkenyl, alkoxy, or hydroxyalkyl of from 5 to 22 carbon atoms each, or aryl or alkanoyl of up to 20 carbon atoms,
$R^6$ is alkyl of from 2 to 6 carbon atoms which may be substituted with a hydroxyl group at the terminal or a non-terminal carbon atom.
Y may be alkylene, optionally interrupted by up to 3 oxygen atoms, of up to 12 carbon atoms, which alkylene chain may optionally be substituted with lower alkyl, alkoxy, hydroxy or hydroxyalkyl, e.g., of not more than 10 carbon atoms each.

Preferably R is a tertiary amine radical of from about 10 to 40 carbon atoms. More preferred are tertiary amine radicals of the type ($C_6$–$C_{20}$ alkyl, dimethyl) amine such as N,N-dimethyl myristylamine, N,N-dimethyl-palmityl-amine, and N,N-dimethyl-laurylamine.

Exemplary tertiary amines having from about 6 to 60 carbon atoms include:
tributylamine,
(di(hydroxyethyl),hexyl)-amine.
tripropylamine,
triisopropanolamine,
bis(2-hydroxyethyl)cocoamine,
polyoxyethylene cocoamine,
bis(2-hydroxy ethyl)soyamine,
polyoxyethylene soyamine,
bis(2-hydroxyethyl)tallow amine,
polyoxyethylene tallowamine,
bis(2-hydroxyethyl)oleylamine,
polyoxyethylene oleylamine,
bis(2-hydroxyethyl)octadecylamine,
polyoxyethylene octadecylamine,
N,N-dimethyl-dodecylamine,
N,N-dimethyl-tetradecylamine,
N,N-dimethyl-hexadecylamine,
N,N-dimethyl-octadecylamine,
N,N-dimethyl-cocoamine,
N,N-dimethyl soya amine, N,N-dimethyl-tallowamine,
N,N-dimethyl-oleylamine,
N-methyl-distearylamine,
tristearylamine,
N,N-dimethyl-(hydrogenated tallow)amine By "tertiary amine" as used herein, applicants refer to amines containing uninterrupted alkyl groups, except for an optional ether atom, and having no functional groups other than hydroxy, illustrated above.

The quaternary compounds of the invention are prepared by reacting the corresponding amine and phosphate triester halide as follows:

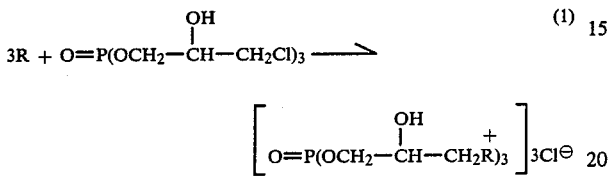

PREPARATION OF INTERMEDIATE "R" REACTANTS

The amine reactant "R" applicable to synthesis (1) is, in general, prepared by reacting an acid with an aminoalkyl-substituted tertiary amine to result in the amidoamine function. Alternatively, an acid can be reacted with an aminoalkyl substituted secondary amine, followed by further treatment of the reaction product with alkylene oxide. Finally, when R represents the N-heterocycle structure, e.g., substituted imidazolinyl, this can be prepared in accordance with known techniques, e.g., as taught in U.S. Pat. No. 2,267,965.

Reaction (2) below yields the non-cyclic reactants "R" and Reaction (3) illustrates the preparation of a typical cyclic amine reactant R (imidazolinyl):

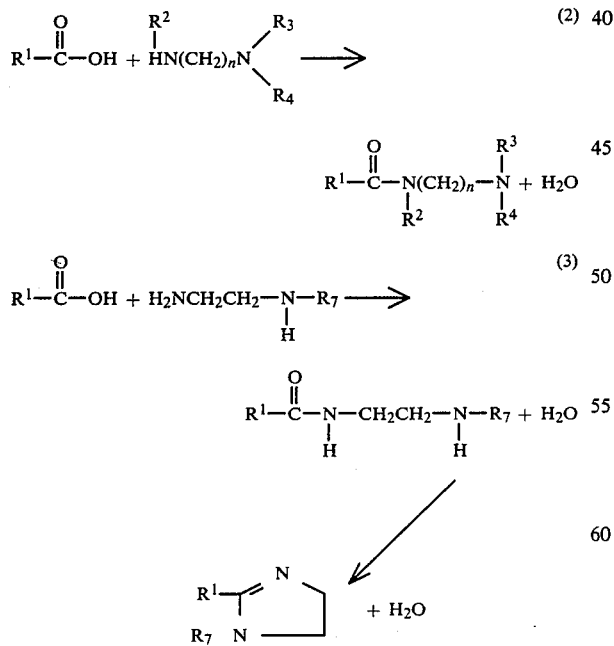

wherein $R^1$ is defined as above and $R^7$ is alkyl of 2 to 6 carbon atoms which may be substituted with a hydroxyl group (at the terminal or a non-terminal carbon atom).

This cyclic reactant can be prepared as disclosed in U.S. Pat. No. 2,267,965.

A vast variety of tertiary amines which are items of commerce are also used for preparation. Alkyl dimethyl amine, di and tri alkyl amines, ethoxylated amines are examples.

PREPARATION OF INTERMEDIATE TRI ESTER REACTANT

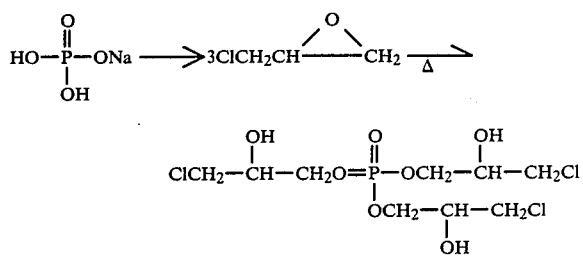

This reactant is prepared via the following method. To 60.00 parts of water charge 12.01 parts of mono sodium phosphate in a suitable reaction vessel under good agitation. Apply heat to 50°–55° C. Slowly charge 27.9 parts epichlorohydrin. Seal reactor and apply 5 psig $N_2$. Heat slowly to 80°–85° C. and hold 2 to 3 hours. Reaction is complete when acid value has been reduced to vanishingly small levels. Inorganic chloride levels will likewise be vanishingly small.

The above reactant was found to be reactive toward certain nucleophilic species, particularly to amines. If an amine of sufficiently hydrophobic character is chosen a surface active agent is obtained when producing in accordance with the invention (Reaction 1) to produce the novel phosphate quaternary compounds.

The compounds of this invention were tested by a "Cylinder Shake Test" for the evaluation of foaming characteristics.

In these test solutions containing 1.1% by weight of the candidate surfactant in water of 100 ppm hardness (calcium to magnesium ratio 3:2) were used and placed in 100 ml stoppered cylinders which had been cleaned so that water drains down its walls in an unbroken film. Each cylinder filled with test solution was shaken twenty (20) times in a standard manner and net foam in ml is noted one minute and again five minutes after shaking. The tests were run in triplicate. The results were as follows:

|  | One Minute | Five Minutes |
|---|---|---|
| Current Products |  |  |
| Cocobetaine | 65 | 56 |
| Cocamidobetaine | 70 | 63 |
| "Monateric CSH-32"* | 66 | 54 |
| Novel Products |  |  |
| Example 5 | 98 | 55 |
| Example 7b | 95 | 89 |

*An amphoteric coco-imidazoline betaine

These novel "MONAQUAT" products attribute viscosity building and conditioning properties as demonstrated by wet comb-out tests.

The novel MONAQUATS were incorporated at 1% active into a standard Baby shampoo formulation (Mona Technical Bulletin No. 960):

TEARLESS BABY SHAMPOO

|  | % By Weight |
|---|---|
| Water | 48.6 |
| Monateric CSH-32 | 40.0 |
| Monateric ISA-35 | 11.4 |
|  | 100.0 |

These formulations were evaluated for (1) viscosity using a Brookfield viscosmeter (spindle #4 at 20 RPMS) and (2) for conditioning properties via a wet comb-out test on hair swatches as per the following procedure.

WET COMB-OUT TEST ON HAIR SWATCHES

Purpose: A laboratory screening method for determining the wet comb-out properties of shampoos under simulated use conditions.

Equipment: Hair swatches are prepared from a purchased supply of human hair from the same head. Each swatch contains 7 grams of hair, 11 inches in length. The hair is tied tightly with string an inch from one end, then bound firmly by wrapping with many laps of adhesive tape. Each swatch is identified by numbering with indelible ink on the tape.

Rat-tail Comb
Stop Watch
Paper Towelling
400 ml Tall Form Beaker

Precleaning Solution: 3% Active Ammonium Lauryl Sulfate

Test Solution: For a shampoo: 10 grams of shampoo in 90 grams tap water.

Procedure:
  (1) Thoroughly wash the swatch by dunking 20 times in the lauryl sulfate precleaning solution.
  (2) Rinse under running tap water at about 40° C., using the spray attachment.
  (3) Squeeze out excess water by drawing the swatch between pinched finger tips.
  (4) Apply the test solution while the hair is still damp by dunking 20 times in 200 ml of test solution at room temperature.
  (5) Rinse with 40° C. running tap water using a spray attachment.
  (6) Excess water is again removed with finger tips.
  (7) Blotting with paper towelling.
  (8) Hang swatch, using opened-out paper clip as hanger.
  (9) While holding the swatch with the finger tips comb swatches as rapidly as possible, on alternate sides, measuring the seconds required with a stop watch.
  (10) Keep combing until the comb passes freely in one long stroke from top to bottom without snagging.
  (11) Observe the time required.

Comments:
  (1) Each test solution should be evaluated with a minimum of three swatches.
  (2) Swatches should be precleaned before each use unless testing for build-up.
  (3) Typical results range from 12-15 seconds for shampoos or rinses with excellent comb-out to 60-75 seconds with poor comb-out properties.

The results were as follows:

| MONAQUAT | VISCOSITY AT pH = 6.5 | TIME IN SECONDS FOR WET COMB-OUT TEST DILUTION 5 g/100 |
|---|---|---|
| Control | 3,700 cps | 31 |
| Example 7d | 10,000 cps | 7 |

The MONAQUAT Compounds, when evaluated by themselves, make good rinse conditioners. Wet comb out tests were conducted using the MONAQUAT at 0.2% active. The following results are typical.

RINSE CONDITIONER (WET COMB OUT TEST)

| Experimental Addition (0.2% Active) | Time in Seconds |
|---|---|
| Example 5 | 11 |
| Example 7b | 14 |
| Example 7d | 9 |
| Control (tap water) | 26 |

As can be seen from the above results, these novel quaternary compounds attribute significant viscosity and conditioning properties. This, in addition to the outstanding foaming properties and low ocular and dermal irritation, makes these products extremely applicable for cosmetics industry.

These products are also admirably suited for use in laundry detergents as softening and antistatic agents. They have excellent compatibility with nonionic and anionic surfactants and may be added directly to the laundry detergent, whereby these softening and antistatic properties can be realized without the need for a separate application of the softening agent in the rinse cycle.

A liquid laundry detergent was prepared having the following composition:

|  | % by Weight |
|---|---|
| Water | 36.5 |
| Triethanolamine | 5.0 |
| Monaterge TM 85[1] | 8.2 |
| Monamine ® ALX-100S[2] | 18.0 |
| Igepal ® CO-630[3] | 30.0 |
| Example 7d | 2.0 |

This formula produced a clear, stable concentrate which was found to give excellent softening and antistatic properties when compared with the same formula without the Monaquat.

1. Mona—A modified Cocamide DEA
2. Mona—A modified Cocamide DEA
3. GAF Corp.—Alkylaryl Nonionic The following examples are presented to show how compounds of the MONAQUAT family can be prepared. They are presented merely for illustration and are not meant to limit the invention.

EXAMPLE #1

To 60.00 parts of soft water in a suitable reactor, charge 12.01 parts of the Reactant under good agitation. Heat to 45°–50° C. and slowly charge 27.99 parts of cocamidopropyl dimethyl amine under good agitation. Heat to 90°–95° C. and hold for 4-5 hours. Reaction is complete when inorganic chloride reaches theoretical and residual tertiary nitrogen levels are vanishingly small.

The product is an aqueous solution of the material shown below:

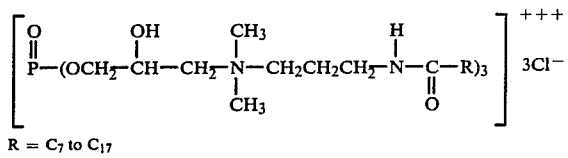

R = C₇ to C₁₇

EXAMPLE #2

To 60.00 parts of soft water in a suitable reactor, charge 12.29 parts of the Reactant under good agitation. Heat to 45°–50° C. and slowly charge 27.71 parts of lauramidopropyl dimethyl amine under good agitation. Heat to 90°–95° C. and hold for 4–5 hours. Reaction is complete when inorganic chloride reaches theoretical and residual tertiary nitrogen levels are vanishingly small.

The product is an aqueous solution of the material shown below:

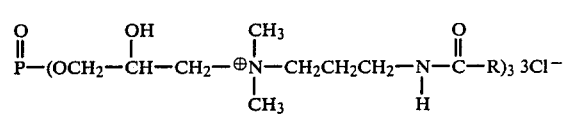

R = C₁₁

EXAMPLE #3

Tp 60.00 parts of soft water in a suitable reactor, charge 11.50 parts of the Reactant under good agitation. Heat to 45°–50° C. and slowly charge 28.50 parts of myristamidopropyl dimethyl amine under good agitation. Heat to 90°–95° C. and hold for 4–5 hours. Reaction is complete when inorganic chloride reaches theoretical and residual tertiary nitrogen levels are vanishingly small.

The product is an aqueous solution of the material shown below:

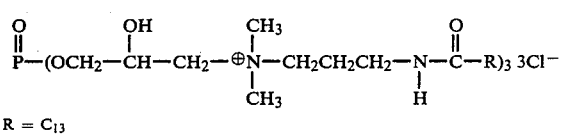

R = C₁₃

EXAMPLE #4

To 60.00 parts of soft water in a suitable reactor, charge 10.19 parts of the Reactant under good agitation. Heat to 45°–50° C. and slowly charge 29.81 parts of stearamidopropyl dimethyl amine under good agitation. Heat to 90°–95° C. and hold for 4–5 hours. Reaction is complete when inorganic chloride reaches theoretical and residual tertiary nitrogen levels are vanishingly small.

The product is an aqueous solution of the material shown below:

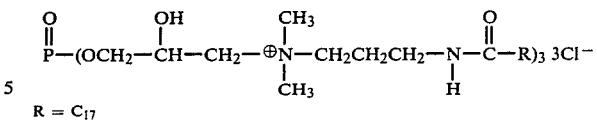

R = C₁₇

EXAMPLE #5

To 60.00 parts of soft water in a suitable reactor, charge 14.28 parts of the Reactant under good agitation. Heat to 45°–50° C. and slowly charge 25.72 parts of alkyl dimethyl amine (alkyl=C₁₂) under good agitation. Heat to 90°–95° C. and hold for 4–5 hours. Reaction is complete when inorganic chloride reaches theoretical and residual tertiary nitrogen levels are vanishingly small.

The product is an aqueous solution of the material shown below:

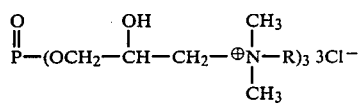

R = C₁₂

EXAMPLE #6

To 60.00 parts of soft water in a suitable reactor, charge 13.22 parts of the Reactant under good agitation. Heat to 45°–50° C. and slowly charge 26.78 parts of alkyl dimethyl amine (alkyl=C₁₄) under good agitation. Heat to 90°–95° C. and hold for 4–5 hours. Reaction is complete when inorganic chloride reaches theoretical and residual tertiary nitrogen levels are vanishingly small.

The product is an aqueous solution of the material shown below:

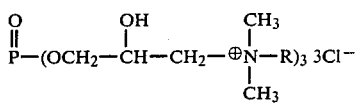

R = C₁₄

EXAMPLE #7

To 60.00 parts of soft water in a suitable reactor, charge 12.32 parts of the Reactant under good agitation. Heat to 45°–50° C. and slowly charge 27.68 parts of alkyl dimethyl amine (alkyl is C₁₆) under good agitation. Heat to 90°–95° C. and hold for 4–5 hours. Reaction is complete when inorganic chloride reaches theoretical and residual tertiary nitrogen levels are vanishingly small.

The product is an aqueous solution of the material shown below:

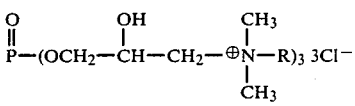

R = C₁₆

EXAMPLE #7a

To 60.00 parts of soft water in a suitable reactor, charge 10.42 parts of the Reactant under good agitation.

Heat to 45°–50° C. and slowly charge 29.58 parts of alkyl hydroxyethyl amine (alkyl is C$_{18}$) under good agitation. Heat to 90°–95° C. and hold for 4–5 hours. Reaction is complete when inorganic chloride reaches theoretical and residual tertiary nitrogen levels are vanishingly small.

The product is an aqueous solution of the material shown below:

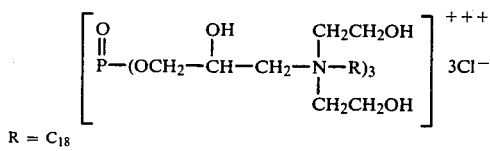

R = C$_{18}$

EXAMPLE #7b

To 60.00 parts of soft water in a suitable reactor, charge 13.22 parts of the Reactant under good agitation. Heat to 45°–50° C. and slowly charge 26.78 parts of alkyl dimethyl amine (alkyl is C$_8$–C$_{18}$) under good agitation. Heat to 90°–95° C. and hold for 4–5 hours. Reaction is complete when inorganic chloride reaches theoretical and residual tertiary nitrogen levels are vanishingly small.

The product is an aqueous solution of the material shown below:

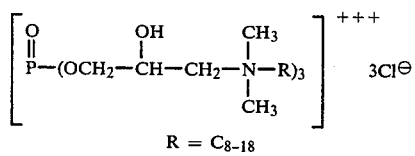

R = C$_{8-18}$

EXAMPLE #7c

To 60.00 parts of soft water in a suitable reactor, charge 13.22 parts of the Reactant under good agitation. Heat to 45°–50° C. and slowly charge 26.78 parts of alkyl diethyl amine (alkyl is C$_{12}$) under good agitation. Heat to 90°–95° C. and hold for 4–5 hours. Reaction is complete when inorganic chloride reaches theoretical and residual tertiary nitrogen levels are vanishingly small.

The product is an aqueous solution of the material shown below:

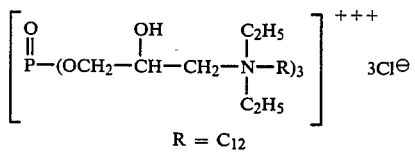

R = C$_{12}$

EXAMPLE 7d

In a suitable reactor place 60.0 parts of water and add with good agitation 11.85 parts of the eactant. Heat to 45°–50° C. and slowly charge 28.15 parts of alkyl dimethyl amine (alkyl is 18) while continuing good agitation. Heat to 90°–95° C. and hold for 4–5 hours. The reaction is complete when the inorganic chloride reaches theoretical and quaternization is achieved.

The product is an aqueous solution of the material shown below:

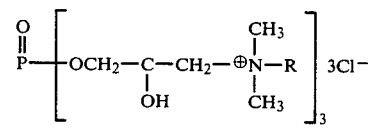

EXAMPLE #8

To 60.00 parts of soft water in a suitable reactor, charge 10.50 parts of the Reactant under good agitation. Heat to 45°–50° C. and slowly charge 29.5 parts of 1-hydroxyethyl-2-alkyl imidazoline (alkyl being C$_{17}$) under good agitation. Heat to 90°–95° C. and hold for 4–5 hours. Reaction is complete when inorganic chloride reaches theoretical and residual tertiary nitrogen levels are vanishingly small.

The product is an aqueous solution of the material shown below:

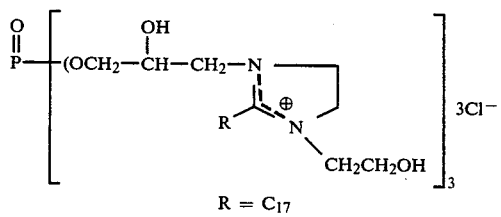

R = C$_{17}$

EXAMPLE #8(a)

To 60.00 parts of soft water in a suitable reactor, charge 14.85 parts of the Reactant under good agitation. Heat to 45°–50° C. and slowly charge 25.15 parts of 1-hydroxyethyl 2-alkyl imidazoline (alkyl being C$_7$) under good agitation. Heat to 90°–95° C. and hold for 4–5 hours. Reaction is complete when inorganic chloride reaches theoretical and residual tertiary nitrogen levels are vanishingly small.

The product is an aqueous solution of the material shown below:

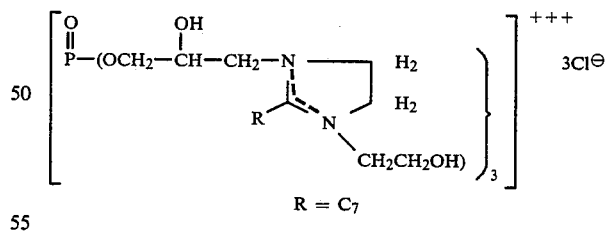

R = C$_7$

EXAMPLE #8(b)

To 60.00 parts of soft water in a suitable reactor, charge 12.73 parts of the Reactant under good agitation. Heat to 45°–50° C. and slowly charge 27.27 parts of 1-hydroxyethyl 2-alkyl imidazoline (alkyl being C$_{11}$) under good agitation. Heat to 90°–95° C. and hold for 4–5 hours. Reaction is complete when inorganic chloride reaches theoretical and residual tertiary nitrogen levels are vanishingly small.

The product is an aqueous solution of the material shown below:

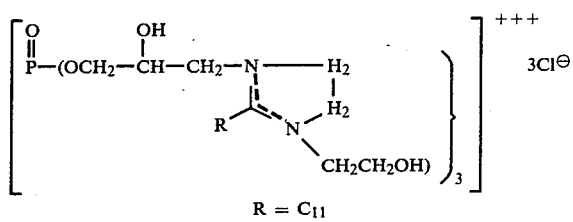

R = C₁₁

EXAMPLE #8(c)

To 60.00 parts of soft water in a suitable reactor, charge 12.0 parts of the Reactant under good agitation. Heat to 45°–50° C. and slowly charge 28.0 parts of 1-hydroxypropyl 2-alkyl imidazoline (alkyl being $C_7$–$C_{17}$) under good agitation. Heat to 90°–95° C. and hold for 4–5 hours. Reaction is complete when inorganic chloride reaches theoretical and residual tertiary nitrogen levels are vanishingly small.

The product is an aqueous solution of the material shown below:

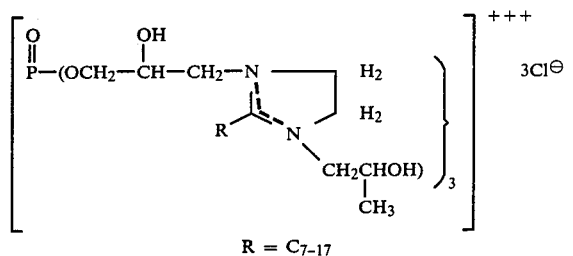

R = C₇₋₁₇

EXAMPLE #9

To 60.00 parts of soft water in a suitable reactor, charge 12.17 parts of the Reactant under good agitation. Heat to 45°–50° C. and slowly charge 27.83 parts of 1-hydroxyethyl 2-alkyl imidazoline (alkyl being $C_7$ to $C_{17}$) under good agitation. Heat to 90°–95° C. and hold for 4–5 hours. Reaction is complete when inorganic chloride reaches theoretical and residual tertiary nitrogen levels are vanishingly small.

The product is an aqueous solution of the material shown below:

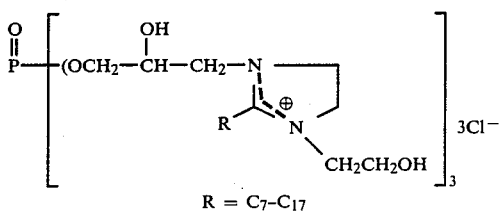

R = C₇–C₁₇

EXAMPLE #10

To 60.00 parts of soft water in a suitable reactor, charge 10.70 parts of the Reactant under good agitation. Heat to 45°–50° C. and slowly charge 29.30 parts of 1-hydroxyethyl 2-alkyl imidazoline (alkyl being $C_{17}$) under good agitation. Heat to 90°–95° C. and hold for 4–5 hours. Reaction is complete when inorganic chloride reaches theoretical and residual tertiary nitrogen levels are vanishingly small.

The product is an aqueous solution of the material shown below:

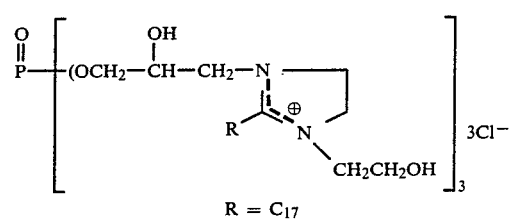

R = C₁₇

EXAMPLE #11

To 60.00 parts of soft water in a suitable reactor, charge 9.72 parts of the Reactant under good agitation. Heat to 45°–50° C. and slowly charge 30.28 parts of N-(alkylamidoethyl)N-hydroxyethyl glycine (alkyl being 70% $C_{11}$/30% $C_{13}$) under good agitation. Heat to 90°–95° C. and hold for 4–5 hours. Reaction is complete when inorganic chloride reaches theoretical and residual tertiary nitrogen levels are vanishingly small.

The product is an aqueous solution of the material shown below:

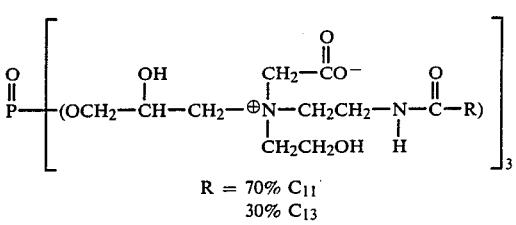

R = 70% C₁₁
30% C₁₃

What is claimed is:

1. Phosphate-quaternary amine compound of the formula

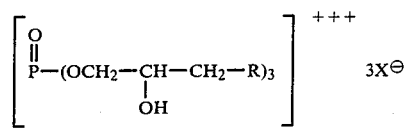

wherein
R is a tertiary amine radical of from 6–40 carbon atoms; and
X is an anion.

2. Compound as claimed in claim 1 wherein R is a tertiary amine radical of from 10–40 carbon atoms.

3. Compound as claimed in claim 1 wherein R is a alkyl-dimethylamine wherein the alkyl moiety has from 6 to 20 carbon atoms.

4. Compound as claimed in claim 3 wherein the alkyl is lauryl.

5. Compound as claimed in claim 3 wherein the alkyl is myristyl.

6. Compound as claimed in claim 3 wherein the alkyl is palmityl.

7. Compound as claimed in claim 1 wherein the tertiary amine radical contains at least one OH group.

8. Phosphate-quaternary amine compound as claimed in claim 1 of the formula

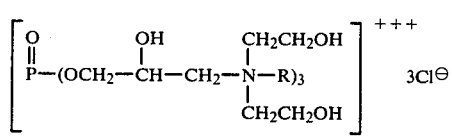

wherein R is stearyl.

9. Phosphate-quaternary amine compound as claimed in claim 1 of the formula

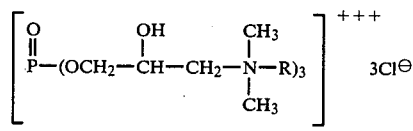

wherein R is cocyl.

10. Phosphate-quaternary amine compound as claimed in claim 1 of the formula

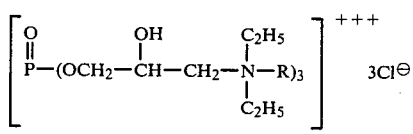

where R is lauryl.

11. Phosphate quaternary amine compounds of the formula:

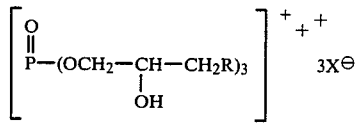

wherein R is:

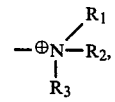

wherein $R_1$, $R_2$, and $R_3$ are the same or different and are alkyl, hydroxyalkyl, carboxyalkyl of up to 6 carbon atoms in each alkyl moiety, polyoxyalkylene of up to 10 carbon atoms, at least one of $R_1$, $R_2$ or $R_3$ contains at least 6 carbon atoms, X is an anion.

* * * * *